United States Patent
Grasso et al.

(10) Patent No.: US 9,107,621 B2
(45) Date of Patent: Aug. 18, 2015

(54) MONITORING OF HEARING PRESERVATION DURING COCHLEAR IMPLANT SURGERY USING STAPEDIAL REFLEX MEASUREMENT

(71) Applicant: MED-EL Elektromedizinische Geraete GmbH, Innsbruck (AT)

(72) Inventors: Peter Grasso, Bolzano (IT); Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/054,898

(22) Filed: Oct. 16, 2013

(65) Prior Publication Data

US 2014/0107441 A1    Apr. 17, 2014

Related U.S. Application Data

(60) Provisional application No. 61/714,263, filed on Oct. 16, 2012, provisional application No. 61/834,983, filed on Jun. 14, 2013.

(51) Int. Cl.
| | | |
|---|---|---|
| *A61N 1/05* | (2006.01) | |
| *A61B 5/12* | (2006.01) | |
| *A61B 5/026* | (2006.01) | |
| *A61N 1/36* | (2006.01) | |
| *A61B 5/0265* | (2006.01) | |
| *A61B 5/145* | (2006.01) | |

(52) U.S. Cl.
CPC ............... *A61B 5/125* (2013.01); *A61B 5/026* (2013.01); *A61N 1/05* (2013.01); *A61N 1/36032* (2013.01); *A61B 5/0265* (2013.01); *A61B 5/14542* (2013.01); *A61N 1/0541* (2013.01)

(58) Field of Classification Search
CPC .................... A61N 1/36032; A61N 1/0541
USPC ............................ 607/55, 57, 137; 128/898
See application file for complete search history.

(56) References Cited

U.S. PATENT DOCUMENTS

| | | | |
|---|---|---|---|
| 6,157,861 A | 12/2000 | Faltys et al. | 607/57 |
| 7,117,038 B1 * | 10/2006 | Overstreet | 607/57 |
| 2007/0179565 A1 | 8/2007 | Overstreet et al. | 607/57 |
| 2011/0066160 A1 | 3/2011 | Simaan et al. | 606/129 |

OTHER PUBLICATIONS

"Temporal Profile of Skeletal Muscle Capillary Hemodynamics During Recovery from Contractions", *Physiology in Press*, published online Mar. 31, 2006 as 10.1113/jphysio1.2006.104801, 38 pages.
International Search Report and Written Opinion—PCT/US2013/065210, date of mailing Jan. 17, 2014, 12 pages.

* cited by examiner

*Primary Examiner* — Paula J Stice
(74) *Attorney, Agent, or Firm* — Sunstein Kann Murphy & Timbers LLP

(57) ABSTRACT

A method is described for surgical implantation of a cochlear implant system. An intraoperative baseline value stapedial reflex response is determined for a cochlear implant patient. Then while performing a given step in a multi-step surgical process to implant a cochlear implant system in the patient, the stapedial reflex response is monitored, and if the stapedial reflex response changes from the baseline value response more than a safe change threshold value, the given step is stopped.

26 Claims, 3 Drawing Sheets

MONITORING OF HEARING PRESERVATION DURING COCHLEAR IMPLANT SURGERY USING STAPEDIAL REFLEX MEASUREMENT

This application claims priority from U.S. Provisional Patent Application 61/714,263, filed Oct. 16, 2012, and U.S. Provisional Patent Application 61/834,983, filed Jun. 14, 2013, which are incorporated herein by reference in their entirety.

TECHNICAL FIELD

The present invention relates to surgical techniques for cochlear implant systems.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant that electrically stimulates auditory nerve tissue with small currents delivered by multiple electrode contacts distributed along an implant electrode. FIG. 1 shows some components of a typical cochlear implant system where an external microphone provides an audio signal input to an external signal processing stage 111 which implements one of various known signal processing schemes. The processed signal is converted by the external signal processing stage 111 into a digital data format, such as a sequence of data frames, for transmission into a receiver processor in an implant housing 108. Besides extracting the audio information, the receiver processor in the implant housing 108 may perform additional signal processing such as error correction, pulse formation, etc., and produces a stimulation pattern (based on the extracted audio information) that is sent through wires in an electrode lead 109 to an implanted electrode array 110. Typically, the electrode array 110 includes multiple electrodes on its surface that provide selective stimulation of the cochlea 104.

The electrode array 110 penetrates into the cochlea 104 through a surgical opening called a cochleostomy. The electrode array 110 has multiple electrode contacts on or slightly recessed below its outer surface for applying one or more electrical stimulation signals to target audio neural tissue within the cochlea 104. The extra-cochlear electrode lad 109 that goes from the implant housing 108 to the cochleostomy opening usually has no electrical contacts except perhaps a ground electrode and it encloses connecting wires that deliver electrical stimulation signals to the electrode contacts on the electrode array 110.

Insertion and placement and insertion of the electrode array 110 into the cochlea 104 causes trauma to the cochlear tissue due to the rigidity, friction, and impact of moving the electrode array 110 through the cochlea 104. For example, insertion of the electrode array 110 may damage soft tissues, membranes, thin bony shelves, blood vessels, neural elements, etc. In the case of multiple insertions, the damage can accumulate. In addition, removal and replacement of the electrode array 110 due to device failure or aging is also a serious problem. For example, patients with some residual hearing now receive hybrid implant systems that also include acoustic-mechanical stimulation components, and further hearing loss could occur when the electrode array 110 is removed or replaced. In addition, there are efforts to use therapeutic drugs to regrow neural tissue around an inserted electrode array 110 which could suffer catastrophic consequences when the electrode is removed since any new neural tissue growth that might reach the electrode could be disrupted or destroyed.

It has been shown that patients with preserved low frequency hearing have significantly better outcomes than those without such hearing preservation. And it is generally accepted that the amount of electrode insertion trauma correlates significantly with the level of hearing loss caused during the surgery. Thus the extent of hearing preservation preoperatively or postoperatively is believed to serve as a good indicator of the magnitude of electrode insertion trauma. See Skarzynski et al., *Atraumatic Round Window Deep Insertion Of Cochlear Electrodes*, Acta Otolaryngol. 2011 July; 131 (7):740-9. Epub 2011 Apr. 15.

Currently there is no existing developed objective method to evaluate intraoperative hearing trauma. There have been some initial proposals of intraoperative methods to detect possible intraoperative trauma, but all of these approaches still are under development. And all of the existing proposals are based on measuring evoked potentials (e.g., ECAPs) either using acoustic stimuli or some combination of electric and acoustic stimuli, and then recording near-field and/or far-field sensor measurements.

Besides evoked potentials such as ECAPs, measurement of the stapedius reflex response also has been widely used in a clinical practice to evaluate hearing and fit hearing prosthesis systems. The stapedius is the smallest skeletal muscle in the human body. At just over one millimeter in length, its purpose is to stabilize the smallest bone in the body, the stapes. The stapedial reflex refers to the involuntary contraction of the stapedius and tensor tympani muscles of the ossicles that occurs in response to a loud sound. The stapedius muscle pulls the stapes (stirrup) of the middle ear away from the oval window of the cochlea and the tensor tympani muscle pulls the malleus (hammer) away from the ear drum. This reflex decreases the transmission of vibrational energy to the cochlea where it is converted into electrical impulses to be processed by the brain for perception as sound.

Several methods to measure the stapedial reflex have been described including:
  Recording a pressure change from a probe placed in the ear canal,
  Recoding a myogenic response in the vicinity of the stapedial muscle or stapedial tendon, and
  Intraoperative surgical observation of the facial nerve during cochlear implant surgery.
In combination with other measurements, measurement of the stapedius reflex can be used to determine if a patient suffers with conductive, sensorineural or mixed hearing loss. However, stapedius reflex responses have not been used for monitoring of hearing trauma during cochlear implant surgery.

SUMMARY

Embodiments of the present invention are directed to a method for surgical implantation of a cochlear implant system. An intraoperative baseline value stapedial reflex response is determined for a cochlear implant patient. Then while performing a given step in a multi-step surgical process to implant a cochlear implant system in the patient, the stapedial reflex response is monitored, and if the stapedial reflex response changes from the baseline value response more than a safe change threshold value, the given step is stopped.

The stapedial reflex response may continue to be monitored after stopping the given step, and the given step may be continued if the response change returns to less than the safe change threshold value. The stapedial reflex response may be determined again after completing the given step, and compared to the baseline value response to evaluate hearing trauma resulting from the given step.

The safe change threshold value may be, for example, a 30% change from the intraoperative baseline response. The stapedial reflex response may be determined based on measuring change of stapedial muscle blood flow or oxygen. The stapedial reflex response may include response amplitude growth and response latency. Either an acoustic stimulus or a bone conduction stimulus may be used to produce the stapedial reflex response. Examples of the given step include insertion of a stimulation electrode into the cochlea of the patient, performing a cochleostomy, and drilling a bone well for an implantable processor.

DETAILED DESCRIPTION

Embodiments of the present invention provide useful real time intraoperative feedback to minimize mechanical trauma during insertion of the cochlear implant electrode. This helps evaluate each surgical step and maneuver in terms of surgical trauma that is measured as a level of frequency specific hearing preservation. The real time feedback also can provide the basis for a surgical navigation tool for use during the electrode insertion. After gentle electrode maneuvers, if the responses get smaller, the electrode can be drawn back slightly and after waiting a brief period for the response to recover, the surgeon can continue trying different maneuvers with the electrode.

Various embodiments of the present invention are directed to use of a modified stapedial reflex response measurement to monitor hearing preservation during cochlear implant surgery. Measurement of stapedial reflexes can be relatively quick and the measured responses are very robust, thus stapedial reflex response can be used as a real-time measurement with no need to determine average response. Unlike other measurement strategies, stapedial reflex responses are measurable at low frequencies and thus are very suitable for measurement of surgical-related hearing trauma, and specific information can be obtained about hearing preservation. But existing clinical methods of measuring the stapedial reflex response cannot be used for intraoperative monitoring of hearing trauma. The described intraoperative measurement depends on the measurement of amplitude growth and stapedial reflex latencies, using different specific stimuli and comparing the obtained information with a baseline intraoperative stapedial reflex measurement.

Figure 1:
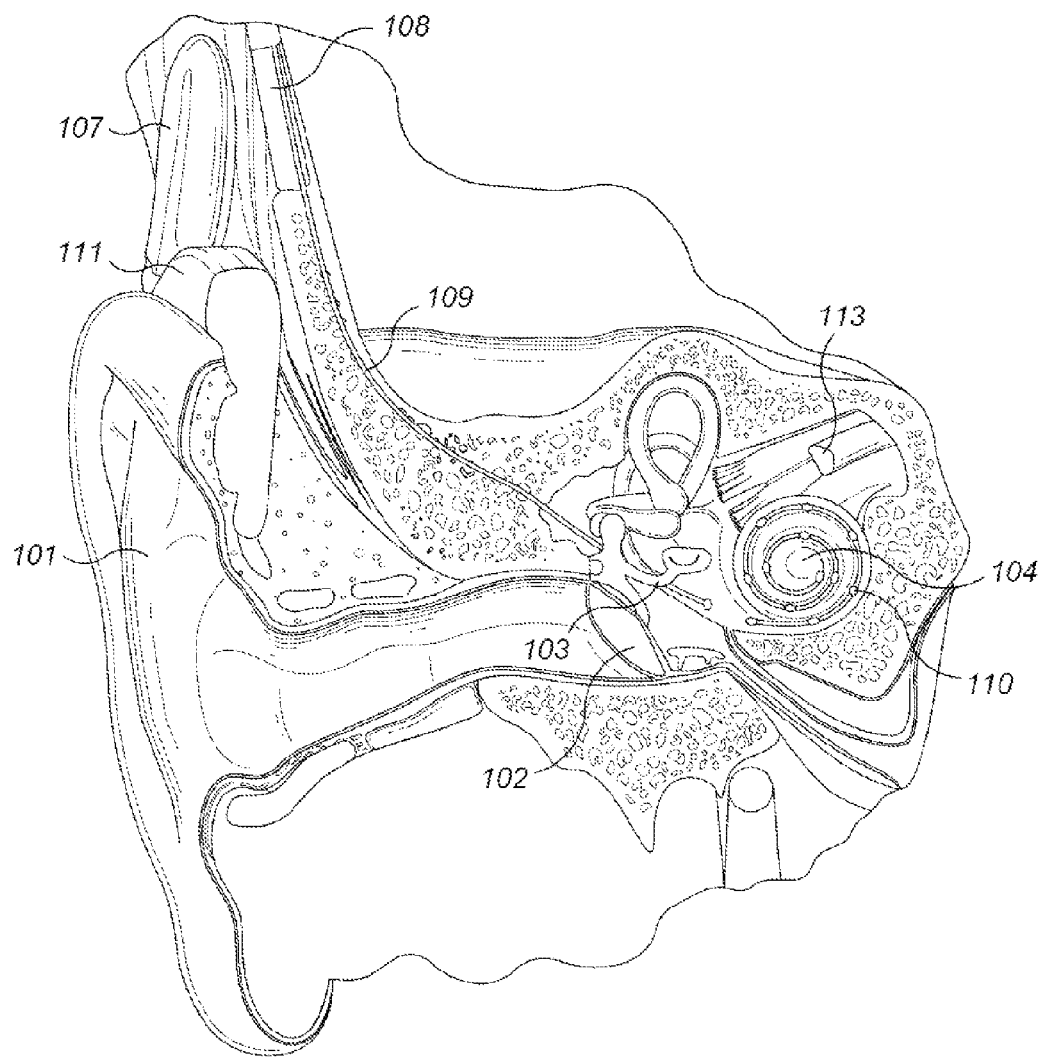
FIG. 1 shows various anatomical structures of the human ear and components of a typical cochlear implant system in relation thereto.
Figure 2:
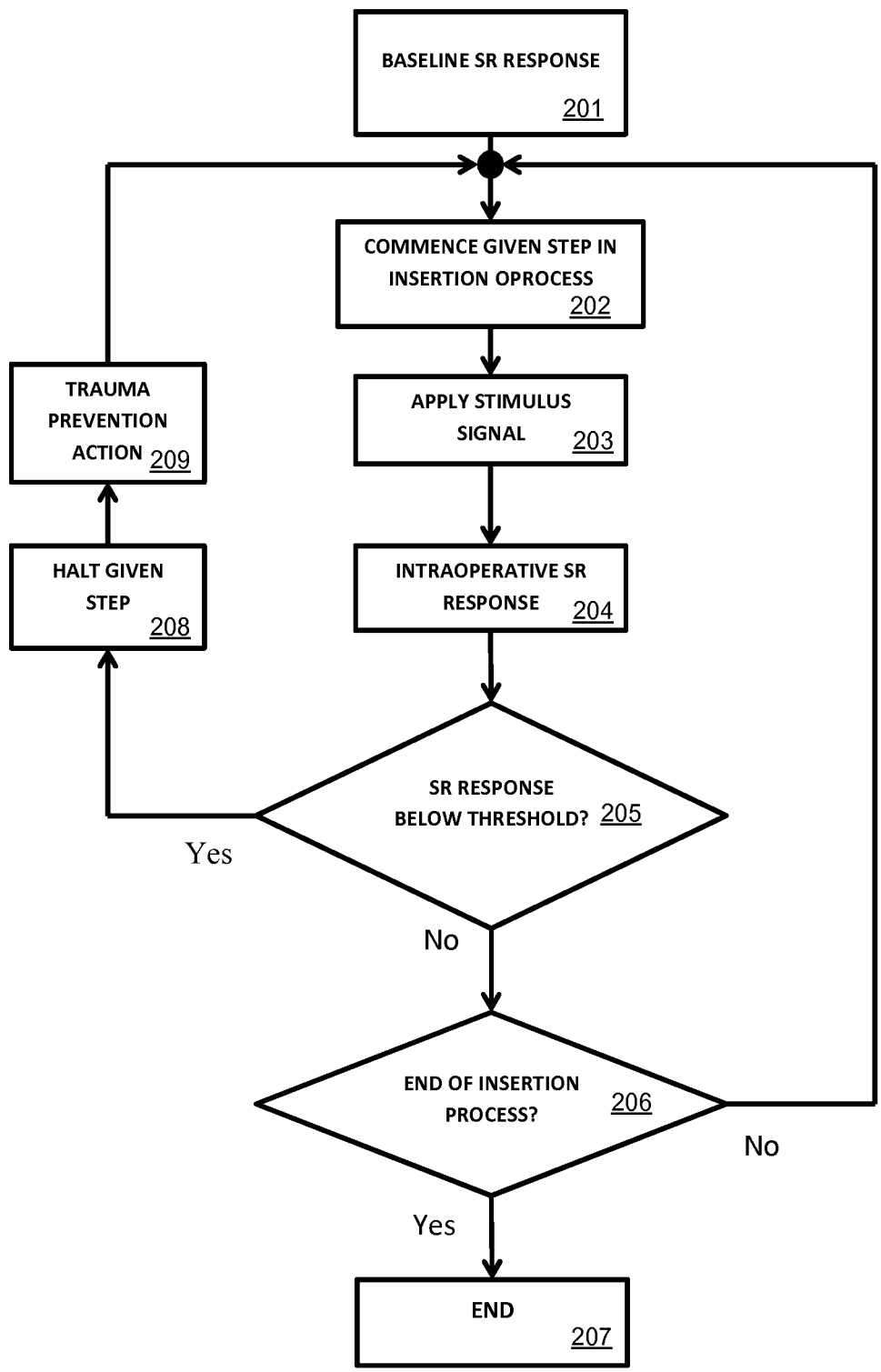
FIG. 2 shows various functional blocks in a method for intraoperative measurement of stapedius reflex responses according to an embodiment of the present invention.

FIG. 2 shows various functional blocks in a method for intraoperative measurement of stapedial reflex responses. Initially, an intraoperative baseline value stapedial reflex response is determined for a cochlear implant patient, step 201. Then the multi-step surgical process commences to implant a cochlear implant system in the patient. At one or more of the specific steps in the process (e.g., insertion of a stimulation electrode into the cochlea of the patient, performing a cochleostomy, and drilling a bone well for an implantable processor) step 202, a stimulus signal is applied, step 203, and the stapedial reflex response is monitored, step 204. If the stapedial reflex response changes from the baseline value response more than a safe change threshold value (e.g., more than 30% change) step 205, then the given step is stopped, (e.g., electrode insertion is stopped) step 208 and trauma preventive action can be performed, step 209. For example, the stapedial reflex response may continue to be monitored after stopping the given step, and the given step may be continued if the response change returns to less than the safe change threshold value. Otherwise, if the stapedial reflex response does not change from the baseline value response more than a safe change threshold value, step 205, then the given step in the surgical process continues until completed, and if the insertion process continues, step 206, the process repeats until all the steps have completed and the process ends, step 207. The stapedial reflex response may be determined again after completing the given step, and compared to the baseline value response to evaluate hearing trauma resulting from the given step.

During such real time monitoring of the stapedial reflex response, the surgeon is immediately notified if some substantial change occurs in the response (e.g., in the response amplitude). Based on the monitoring information, the surgeon can decide whether to continue or stop the current surgical step. For example, if the stapedial reflex amplitude and latency changed by 30%, the surgeon may be asked to stop performing the current surgical step (e.g., stop drilling, stop opening the cochlea, etc.) In the case of electrode insertion, the surgeon can stop inserting and gently withdraw the electrode array a small amount. After some time has elapsed, when the stapedial reflex amplitude returns to baseline or becomes stable and reliable again, the surgeon may continue. By giving this information to the surgeon quickly, surgically related hearing trauma can be expected to be reduced.

During some or all of the specific surgical steps (such as cochleostomy or drilling), a full battery test that gives frequency dependent information about hearing trauma may not be necessary. Rather, one stimulus (e.g., broadband noise and/or tone bursts) can be tested. For simplification, only broadband noise at a few different amplitudes need be tested. One advantage of using broadband noise stimulus signals is high sensitivity to stapedial reflex amplitude and stapedial reflex threshold change.

After the surgical process is complete (i.e., after the electrode is in place), a final measurement of the stapedial reflex can be performed and compared with the baseline measurement to evaluate the total hearing trauma due to the surgery. That is, an approximate frequency dependent hearing loss for each specific frequency can be stated based on subtracting from the baseline and final stapedial reflex responses to determine an approximate total hearing loss.

Figure 3:
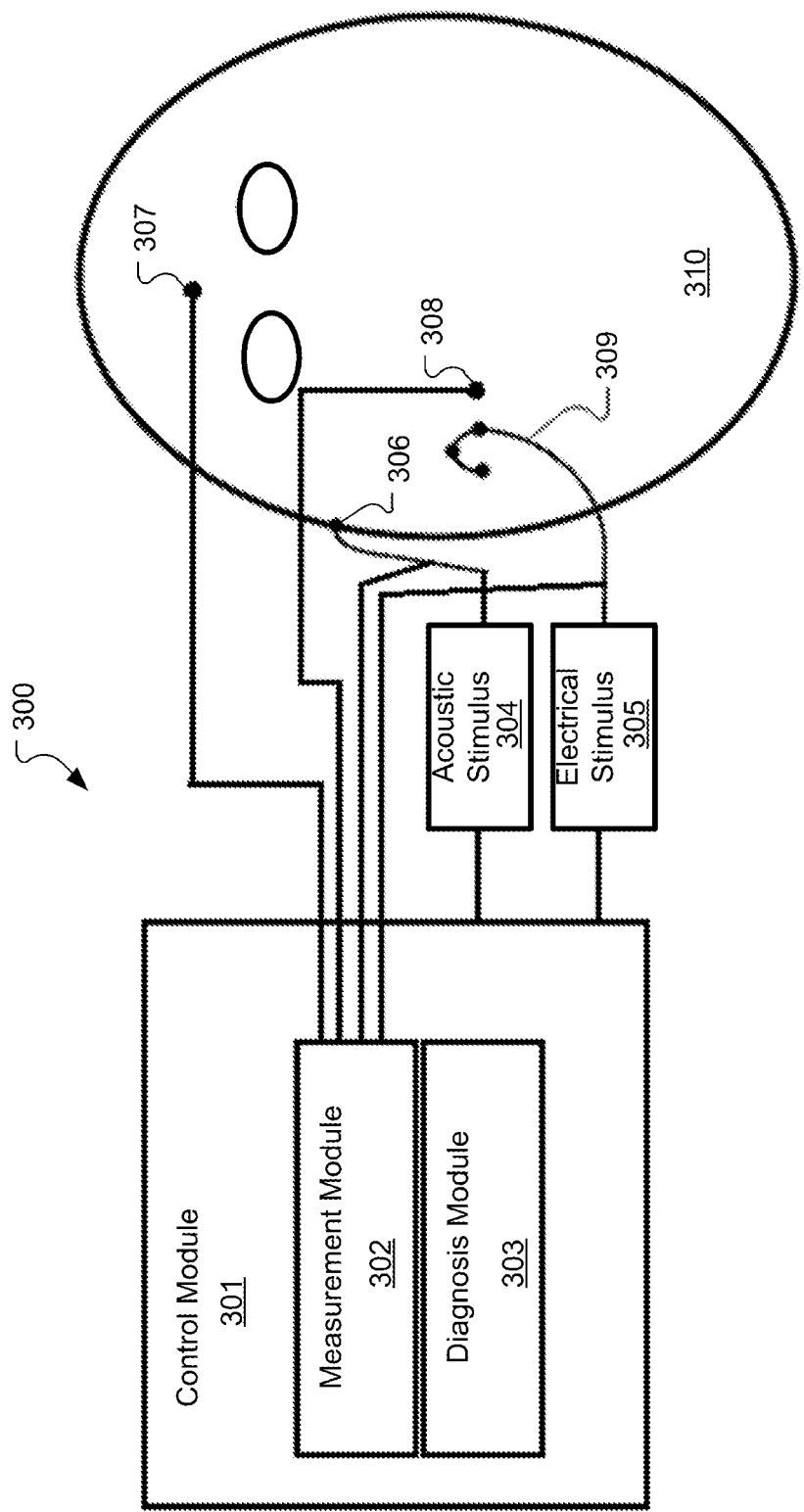
FIG. 3 shows an arrangement for intraoperative measurement of stapedial reflex responses.

FIG. 3 shows an arrangement for intraoperative measurement of stapedial reflex responses in a cochlear implant patient 310. A control module 301 can be a regular audiometer module configured for acoustic stimulation and recordings (e.g., based on the Med-El Maestro diagnostic module). The control module 301 directs acoustic stimulation module 304 to deliver acoustic stimulus signals to the ear canal of the patient 310 to evoke a stapedius reflex response. For example, the acoustic stimulation can be performed on the ipsilateral side ear canal with an inserted ear phone 306. Electrical stimulation module 305 represents the components of the cochlear implant system being implanted along with its electrode array 309. The stimulus signals of the acoustic stimulation module 304 and the electrical stimulation module 305 also are measured as an input to a stapedius reflex response measurement module 302 of the control module 301. The stapedius reflex response measurements are made by one or more recording electrodes 308 (e.g., bipolar microwire electrodes) and in combination with a reference electrode 307. The recording electrodes 308 (+ and −) can be positioned around the stapedius tendon. Sensor or bipolar electrodes also can be attached to the cochlear implant electrode 309. The reference electrode 307 can be the housing of the cochlear implant processor or a distant electrode placed, for example, in the muscle temporalis 310. The reference electrode also can be a surface electrode, i.e placed on the lower forehead of the patient.

There are several different ways to evoke stapedial reflexes. Most typically, the stimulation of stapedial muscle can be evoked acoustically. Tympanometry records changes in middle ear immittance while air pressure is varied in the ear canal and stapedial reflexes are recorded at a single air pressure setting from either the ipsilateral or contralateral side. Alternatively, bone conduction may be sued to apply the stimulus signals. Such a measurement may provide more insight into the origin of the hearing loss (i.e. conductive or sensorineural hearing loss).

The acoustic stimulus signals may be broadband noise signals and/or various tone bursts (e.g., 0.5 kHz, 1 kHz, 2 kHz, 4 kHz) at various amplitudes. For n different frequencies, at least two different pure tone frequencies maybe applied, and in addition, a broadband noise and/or chirp stimulus also may be used. Typical duration of the acoustic stimuli is 300-500 msec. Tone bursts are typically in the range of 250-2000 Hz and can be selected based on the preoperative baseline audiogram for the patient.

Measurement of EMG potentials can be detected by a stapedius sensor or bipolar recording electrodes inserted in the stapedius tendon in the middle ear. In addition or alternatively, visual observation of the stapedial muscle may be used. The amplitude of the stapedius reflex response, response latency, and timing (sustained or rapidly decaying) can be quantified. Typical reflex latencies in normal subjects range from 40-180 milliseconds, typically around 107 milliseconds, and normally the reflex response does not decay.

The critical percentage change of level of stapedial reflex amplitude and stapedial reflex latency (i.e. 30%) may vary from patient to patient according to individual hearing sensitivity and retrocochlear function. The range for acoustic reflexes in individuals with normal hearing averages 70-100 decibel (dB) sound pressure level (SPL). The greater the hearing loss, the higher the acoustic reflex threshold for conductive hearing loss. For sensorineural hearing loss, acoustic reflex thresholds may be within the normal range, particularly for mild-to-moderate hearing losses with recruitment. Elevated or absent acoustic reflex thresholds (i.e., >100 dB SPL) for any given frequency may suggest sensorineural or conductive hearing loss, facial nerve disorder, or middle ear disorder. Reflexes usually are absent or cannot be recorded if the patient has type B tympanograms and so acoustic reflexes generally are not tested in such patients.

Amplitude growth up to 20 dB above the stapedius reflex threshold will be approximately linear both for tone bursts (500 Hz, 1 kHz, 2 kHz, etc.) and for broad band stimuli. Recordings of myogenic potential may be more sensitive than commercially available measurement via change of the air pressure on the eardrum. Stapedius reflex thresholds are lowest for broadband stimuli; comparing normal hearing patients and patients with sensorineural hearing loss of 30-70 dB, the difference of average stapedial reflex threshold is 18 dB. Moreover, effective measurement of stapedius reflex responses is achievable in a large population—approximately 80% of patients with sensorineural hearing loss of less than 80 dB have an elicitable stapedial reflex threshold, and approximately 95% of patients with sensorineural hearing loss of less than 60 dB have and elicitable stapedial reflex threshold (requiring stimulation up to 125 dB).

But stapedial reflex thresholds do not increase linearly with the amount of sensorineural hearing loss. For tone burst stimuli of both normal hearing patients and patients with sensorineural hearing loss of 30-70 dB, the average amplitude growth does not significantly change (use of tone bursts may not be sensitive enough to judge the level of hearing trauma). And when using only broadband stimuli, frequency-specific information may not be obtainable. During the intraoperative measurement, the middle ear structure needs to be undisturbed and fully functioning. Using recordings of EMG can achieve more sensitive and precise outcomes than measuring middle ear air pressure. For bilateral patients it may be easier to use ipsilateral recordings (as opposed to the widely used eSRT method) and thereby avoid influence from the contralateral ear. The responses may be recorded using bipolar microwire electrodes that are positioned around the stapedial tendon. This leads to a favorable S/N ratio.

There have been reports describing attempts to measure cochlear blood flow. But there is no report of using such a blood flow measurement to measure the stapedial reflex response to sound stimulus (acoustic, mechanical or electric). Embodiments of the present invention do just that. When the stapedius muscle is at rest, blood flow through it is at some "normal" baseline level. As soon as the stapedial reflex muscle contraction starts, the blood flow through the muscle increases by a factor of ten or more. Stapedial muscle blood flow remains high for several hundred milliseconds as the reflex contractions end, but then returns back toward the normal baseline flow during the next few hundred milliseconds.

Placing a blood flow probe in the vicinity of the stapedial muscle or tendon, this change in blood flow can easily be measured and recorded. The blood flow probe may specifically be a laser doppler probe that be made in a very small diameter (e.g., 0.8 mm), which is easy to use during the surgical intervention. For reliable measurements, the blood flow probe needs to be kept stable and secure at a controlled fixed position in the vicinity of the stapedial muscle or stapedial tendon. Since the blood flow change occurs at the initial state of the stapedial muscle contraction, the surgeon can be informed of the stapedial response at a stimulus level before the stapedial reflex conventionally can be observed by pressure change from a probe placed in the ear canal.

In addition to the forgoing discussion of changes in blood flow signalling occurrence of the stapedius reflex, there also is a good correlation between increased blood flow increases and an increase in the amount of oxygen consumed during the muscle contraction. Because oxygen is consumed by a muscle when it contracts, the oxygen concentration in the tissue fluids decreases. This causes local arteriolar vasodilation both because arteriolar walls cannot maintain contraction in the absence of oxygen, and because oxygen deficiency causes release of vasodilator substances (e.g., Adenosine, K+ ions, ATP, lactic acid, carbon dioxide). That process can be effectively recorded by a device measuring the oxygen change.

There have been reports attempting to measure such changes in oxygen level, but not to measure the stapedial reflex response to sound stimulus (acoustic, mechanical or electric). Embodiments of the present invention can be based on measuring such changes in oxygen level in the blood from the stapedius muscle; specifically, the decreased concentration of oxygen in the stapedial tissue that occurs when the muscle contracts. When the stapedius muscle is at rest, oxygen concentration in the tissues is at some "normal" baseline level. As soon as the stapedial reflex muscle contraction starts, the oxygen consumption by the muscle increases by a factor of ten or more, which can easily be measured.

This is achieved by using an oxygen probe being placed in the vicinity of the stapedial muscle in a controlled manner. There are several specific ways to measure the oxygen level such as by using an oxygen sensor. For reliable measurements, the oxygen sensor needs to be kept stable and secure at a controlled fixed position in the vicinity of the stapedial muscle or stapedial tendon. Since the oxygen level change occurs at the initial state of the stapedial muscle contraction, the surgeon can be informed of the stapedial response at a stimulus level before the stapedial reflex conventionally can be observed by pressure change from a probe placed in the ear canal.

Although various exemplary embodiments of the invention have been disclosed, it should be apparent to those skilled in the art that various changes and modifications can be made which will achieve some of the advantages of the invention without departing from the true scope of the invention.

What is claimed is:

1. A surgical arrangement for implantation of a cochlear implant system, the arrangement comprising:
   means for determining an intraoperative baseline value stapedial reflex response for a cochlear implant patient; and
   means for monitoring a given step in a multi-step surgical process to implant a cochlear implant system in the patient, the means for monitoring being configured to:
   a. monitor a stapedial reflex response produced in response to an evoking stimulus, and
   b. recommend stopping the given step if the stapedial reflex response changes from the baseline value response more than a safe change threshold value.

2. The surgical arrangement according to claim 1, wherein the means for monitoring is further configured to:
   c. continue to monitor the stapedial reflex response after stopping the given step, and
   d. recommend continuing the given step if the response change returns to less than the safe change threshold value.

3. The surgical arrangement according to claim 1, wherein the means for monitoring is further configured to:
   determine the stapedial reflex response after completing the given step; and
   compare the stapedial reflex response determined after completing the given step to the baseline value response to evaluate hearing trauma resulting from the given step.

4. The surgical arrangement according to claim 1, wherein the safe change threshold value is a 30% change from the intraoperative baseline response.

5. The surgical arrangement according to claim 1, wherein the stapedial reflex response is determined based on measuring change of stapedial muscle blood flow.

6. The surgical arrangement according to claim 1, wherein the stapedial reflex response is determined based on measuring change of stapedial muscle oxygen.

7. The surgical arrangement according to claim 1, wherein the stapedial reflex response includes response amplitude growth and response latency.

8. The surgical arrangement according to claim 1, wherein an acoustic stimulus is used for producing the stapedial reflex response.

9. The surgical arrangement according to claim 1, wherein a bone conduction stimulus is used for producing the stapedial reflex response.

10. The surgical arrangement according to claim 1, wherein the given step is insertion of a stimulation electrode into a cochlea of the patient.

11. The surgical arrangement according to claim 1, wherein the given step is performing a cochleostomy.

12. The surgical arrangement according to claim 1, wherein the given step is drilling a bone well for an implantable processor.

13. A method for surgical implantation of a cochlear implant system, the method comprising:
    determining an intraoperative baseline value stapedial reflex response for a cochlear implant patient; and
    while performing a given step in a multi-step surgical process to implant a cochlear implant system in the patient:
    a. monitoring a stapedial reflex response produced in response to an evoking stimulus, and
    b. if the stapedial reflex response changes from the baseline value response more than a safe change threshold value, stop performing the given step.

14. The method according to claim 13, further comprising:
    c. after stopping the given step, continuing to monitor the stapedial reflex response, and
    d. if the response change returns to less than the safe change threshold value, continuing the given step.

15. The method according to claim 13, further comprising:
    determining the stapedial reflex response after completing the given step; and
    comparing the post-step response to the baseline value response to evaluate hearing trauma resulting from the given step.

16. The method according to claim 13, wherein the safe change threshold value is a 30% change from the intraoperative baseline response.

17. The method according to claim 13, wherein the stapedial reflex response is determined based on measuring change of stapedial muscle blood flow.

18. The method according to claim 13, wherein the stapedial reflex response is determined based on measuring change of stapedial muscle oxygen.

19. The method according to claim 13, wherein the stapedial reflex response includes response amplitude growth and response latency.

20. The method according to claim 13, wherein an acoustic stimulus is used for producing the stapedial reflex response.

21. The method according to claim 13, wherein a bone conduction stimulus is used for producing the stapedial reflex response.

22. The method according to claim 13, wherein the given step is insertion of a stimulation electrode into a cochlea of the patient.

23. The method according to claim 13, wherein the given step is performing a cochleostomy.

24. The method according to claim 13, wherein the given step is drilling a bone well for an implantable processor.

25. A method of determining stapedius reflex response comprising:
- measuring a baseline blood flow to a stapedius muscle in an absence of a sound stimulus;
- applying a sound stimulus at a given level;
- measuring blood flow to the stapedius muscle;
- increasing the level of the sound stimulus and repeating the steps of applying and measuring until an increase occurs in the measured blood flow indicating occurrence of a stapedius reflex response.

26. A method of determining stapedius reflex response comprising:
- measuring a baseline oxygen level in a stapedius muscle in an absence of a sound stimulus;
- applying a sound stimulus at a given level;
- measuring oxygen level in the stapedius muscle;
- increasing the level of the sound stimulus and repeating the steps of applying and measuring until a decrease occurs in the measured oxygen level indicating occurrence of a stapedius reflex response.

* * * * *